US005770756A

United States Patent [19]

Blake et al.

[11] Patent Number: 5,770,756

[45] Date of Patent: Jun. 23, 1998

[54] HIGHLY CONCENTRATED ALKYL SULPHATE SOLUTIONS

[75] Inventors: Alan David Blake, Overijse; Jozef Philomena Geudens, Zellik; Peter Geoffrey Mather, Brussels, all of Belgium

[73] Assignee: The Procter & Gamble Company, Cincinnati, Ohio

[21] Appl. No.: 500,910

[22] PCT Filed: Jan. 28, 1994

[86] PCT No.: PCT/US94/01023

§ 371 Date: Nov. 14, 1995

§ 102(e) Date: Nov. 14, 1995

[87] PCT Pub. No.: WO94/18160

PCT Pub. Date: Aug. 18, 1994

[30] Foreign Application Priority Data

Feb. 4, 1993 [EP] European Pat. Off. .............. 93200287

[51] Int. Cl.$^6$ ........................ C07C 305/06; C07C 305/10

[52] U.S. Cl. ................................ 558/43; 558/31; 558/34; 558/38; 558/39

[58] Field of Search ................................ 558/31, 34, 38, 558/39, 43

[56] References Cited

U.S. PATENT DOCUMENTS

| | | | |
|---|---|---|---|
| 3,305,578 | 2/1967 | Maurer et al. .......................... | 260/459 |
| 4,645,627 | 2/1987 | van Paassen et al. . | |

*Primary Examiner*—Nicky Chan
*Attorney, Agent, or Firm*—Ken K. Patel; Jacobus C. Rasser; Jerry J. Yetter

[57] ABSTRACT

A process for making high active alkyl sulphate solutions comprising premixing alcohol and/or alkoxylated nonionic surfactant with an organic amine and adding sulfuric acid to the premix to produce a neutralized product having substantially no water is provided. The weight ratio of the sulfuric acid additive to the premix is from 0.5:1 to 9:1.

8 Claims, 1 Drawing Sheet

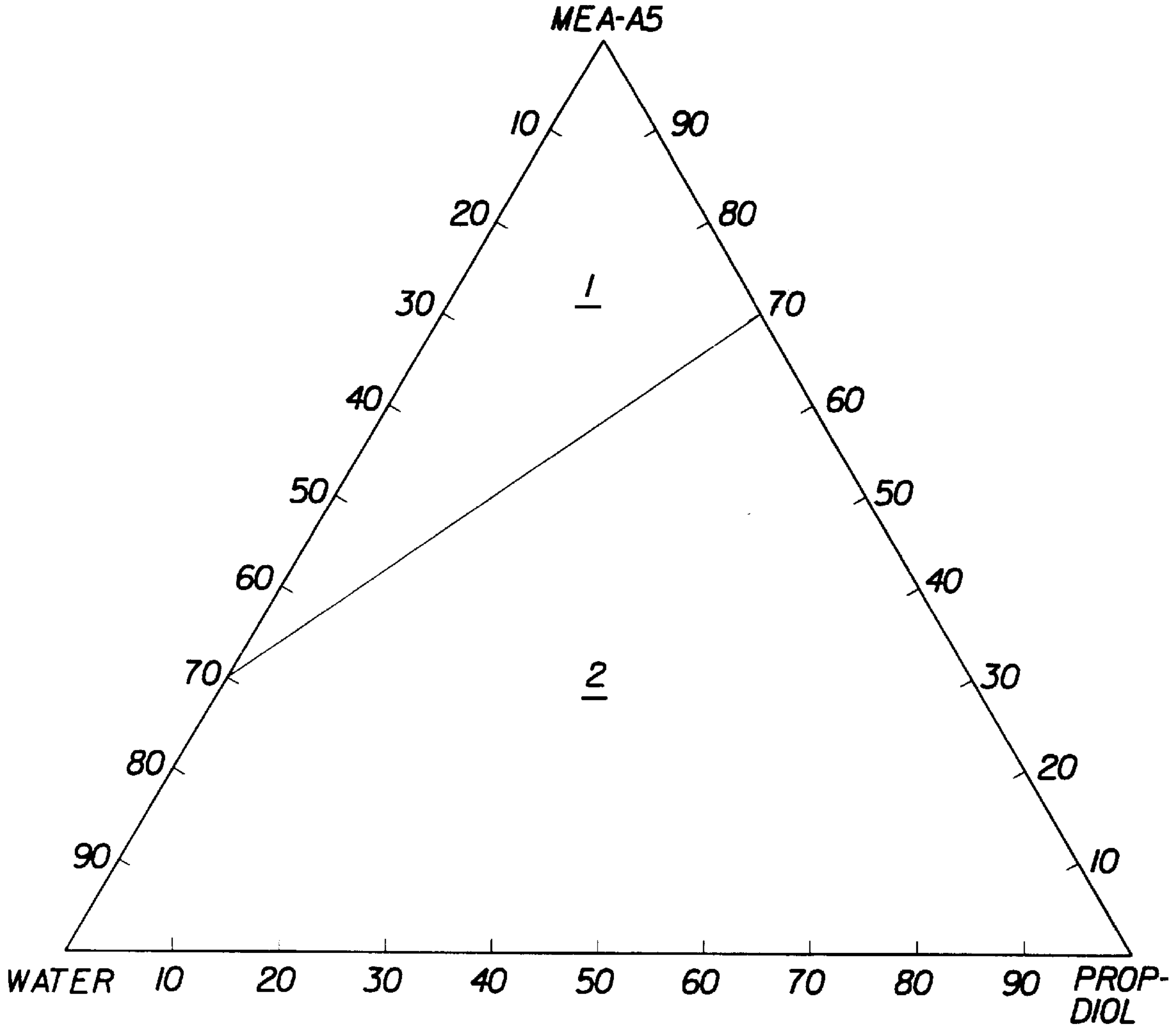
MEA-A5
10
20
30
40
50
60
70
80
90
90
80
70
60
50
40
30
20
10
1
2
WATER
10
20
30
40
50
60
70
80
90
PROP-
DIOL

HIGHLY CONCENTRATED ALKYL SULPHATE SOLUTIONS

This application is a 371 of PCT/US94/01023 filed Jan. 28, 1994, published as WO94/18160 Aug. 18, 1994.

TECHNICAL FIELD

The present invention relates to the manufacture of high active alkyl sulphate solutions.

BACKGROUND OF THE INVENTION

Currently, there is high interest to provide high active surfactant solutions. These products would provide advantages to the consumer, who has a product which can be used in lower amounts, and to the producer, who has lower shipping costs.

In the manufacture of highly concentrated alkyl sulphates solutions neutralization is conventionally affected with aqueous solutions of neutralizing agents.

A major difficulty, though, is finding an inexpensive and efficient way to produce said high active sulphate solution.

It has generally been found that the total concentration of active material was limited up to critical levels. At the critical level the solution sets into an immobile gel or phase separation occurs. It is well known in the art, to use flow aids and viscosity modifiers so that higher concentrations can be attained. Such processing aids can adversely affect the properties of the end product and increases the cost of the product.

We have now discovered that it is possible to increase the concentration of active material by reacting alkylsulphates with organic amines in a neutralization system.

According to the process of the present invention, a highly concentrated alkyl sulphate solution is provided, which is isotropic and freeflowing at room temperature without the need of adding cosolvents or viscosity modifiers. According to one embodiment of the present invention a process is provided in which alcohol and/or nonionic surfactants are added during neutralization. According to another embodiment, a highly concentrated mixture of alkylsulphate and alkyl ether sulphate solution is provided.

SUMMARY OF THE INVENTION

The present invention relates to a process for producing isotropic high active alkyl sulphate solutions, comprising the steps of adding and mixing an alkyl sulfuric acid having a chain length of $C_{12}$-$C_{18}$, with an organic amine to produce a neutralized product having substantially no water.

According to another embodiment of the present invention, the present invention relates to a process for producing high active alkyl sulphate solutions in which alcohol and/or nonionic surfactants are added during neutralization.

BRIEF DESCRIPTION OF THE DRAWING

The Figure shows a phase diagram drawn from the data provided in Table 1 for monoethanolamine (MEA), 1,2 propanediol, and water wherein structured liquid 1 and isotropic liquid 2 are shown.

DETAILED DESCRIPTION OF THE INVENTION

The present invention relates to a process for producing isotropic high active alkyl sulphate solutions, comprising the steps of adding and mixing an alkyl sulfuric acid having a chain length of $C_{12}$-$C_{18}$, with an organic amine to produce a neutralized product having substantially no water.

The $C_{12-18}$ alkyl sulfuric acid can be made by any sulfation process, but preferably are sulfonated with $SO_3$ in air in a falling film reactor. The alkyl sulfate can be obtained from alifatic alcohols with an average from 12–18 carbon atoms, produced by reaction of a triglyceride obtained from animal fat or palm oil and sulfonation of the alifatic alcohol. Preferred alkylsulfuric acids are produced from $C_{12}$-$C_{14}$ natural fatty alcohol and $C_{12}$-$C_{15}$ synthetic fatty alcohol.

The alkyl sulfuric acid may be present as such or as a mixture with other compounds. Examples of such compounds are alkyl alkoxylated sulfuric acids. In this case, the process according to the present invention provides a mixture of high active alkyl sulfate and alkyl ether sulfate solutions. Suitable alkyl alkoxylated sulfuric acids include acids of the formula $RO(A)_mSO_3H$, wherein R is an unsubstituted $C_{10}$-$C_{24}$ alkyl or hydroxyalkyl group having a $C_{10}$-$C_{24}$ alkyl component, preferable a $C_{12}$-$C_{20}$ alkyl or hydroxyalkyl, more preferably $C_{12}$-$C_{18}$ alkyl or hydroxyalkyl ; A is an ethoxy or propoxy unit; m is greater than zero, typically between 0.5 and 6, preferably between 0.5 and 3.

The organic amine in the process is preferably selected from an alkyl- or alkanolamine or mixtures thereof. More preferable, the alkanolamine used to neutralize the alkyl sulfuric acid is monoethanolamine.

The organic amine is preferably present in slight excess of the stoichiometric amount necessary to neutralize the acid. If reserve alkalinity drops below about 0.1%, the alkyl sulfuric salt may not be stable long term because of hydrolysis. It is therefore preferred that reserve alkalinity, which can be measured by titration with acid, in the neutralization system is present in at least 0.1%, more preferably at least 0.2% and most preferably at least 0.3% by weight of the neutralized salt.

According to this process , an isotropic highly concentrated alkyl sulphate solution is provided, without the need of adding cosolvents or viscosity modifiers.

In accordance with the present invention, there is also a process provided in which alcohol and/or nonionic surfactants are added during neutralization. Suitable nonionic surfactants can be selected from ethoxylated nonionic surfactants of the formula $R(OC_2H_4)_nOH$, wherein R is a $C_{8-18}$ alkyl group and n is from about 1 to 12 or can be selected from polyhydroxy fatty acid amide surfactants or mixtures thereof; The alcohol and/or the nonionic surfactant can be added to neutralizing system as a mixture with the organic amine or can be added as a mixture with the alkylsulfuric acid.

According to this embodiment, the process comprises the following steps : the first step (a) of the process according to the present invention is premixing alcohol and/or ethoxylated nonionic surfactant of the formula $R(OC_2H_4)_nOH$, wherein R is a $C_{8-18}$ alkyl group and n is from about 1 to 12, with an organic amine.

The second step (b) is adding to said premix $C_{12-18}$ alkyl sulfuric acid, to produce a neutralized product having substantial no level of water. The weight ratio of the additive of step (b) to the product of the mixing step (a) is preferably from 0.5:1 to 9:1, more preferably from 1:1 to 2.5:1.

The acid and organic amine/alcohol mixture are put into the neutralization system separately, preferably at the high shear mixer so that they mix together as rapidly as possible.

Preferably, the neutralization reaction according to the present invention is carried out in a loop cooling system.

Generally, in a continuous neutralization loop, the ingredients enter the system through a pump (typically centrifugal) which circulates the material through a heat exchanger in the loop and back through the pump, where new materials are introduced. The material in the system continually recirculates, with as much product exiting as is entering. Product exits through a control valve which is usually after the pump. The circulation rate of a continuous neutralization loop is between about 1:1 and 50:1. The temperature of the neutralization reaction can be controlled to a degree by adjusting the amount of cooling by the heat exchanger. The "througput" can be controlled by modifying the amount of acid and amine introduced. The temperature of the loop should be sufficiently high to maintain the lowest possible viscosity of the mixture to ensure adequate recirculation and mixing. Typical temperatures in the loop are between about 20°–80° C.

Preferred alcohols suitable for the process according to the present invention are alcohols selected from ethanol, propylene glycol or mixtures thereof.

These alcohol and/or the nonionic surfactant are chosen because they enhance detergent performance and/or finished product stability while being at the same time processing aids by reducing the viscosity of the high active paste in the neutralizer loop.

The alcohol and/or nonionic surfactants are conventionally used as detergent ingredients and are usually added to the detergent matrix by mixing with the other coingredients. Incorporating these components at the neutralizing step allows the formulation of highly active alkyl sulfate solutions without the need of the adding of cosolvents and viscosity modifiers.

The alkyl sulfate salt produced according to the process described herinabove, contains substantially no water and are isotropic liquids at room temperature.

As used herein, the term "substantially no water" mean that the amount of water is present only due to impurities. The alkyl sulfate salt is then mixed with the remaining detergent ingredients in the next processing steps to obtain a liquid detergent composition.

Detergent ingredients

In another embodiment of the present invention, a liquid detergent composition is provided comprising the high active alkylsulfate ester mixed with other detergent ingredients. A wide range of surfactants can be used in the detergent composition of the present invention.

A typical listing of anionic, nonionic, ampholytic and zwitterionic classes, and species of these surfactants, is given in U.S. Pat. No. 3,664,961 issued to Norris on May 23, 1972.

One class of nonionic surfactants useful in the present invention are condensates of ethylene oxide with a hydrophobic moiety to provide a surfactant having an average hydrophilic-lipophilic balance (HLB) in the range from 8 to 17, preferably from 9.5 to 13.5, more preferably from 10 to 12.5. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

Especially preferred nonionic surfactants of this type are the $C_9$-$C_{15}$ primary alcohol ethoxylates containing 3–8 moles of ethylene oxide per mole of alcohol, particularly the $C_{14}$-$C_{15}$ primary alcohols containing 6–8 moles of ethylene oxide per mole of alcohol and the $Cl_2$-$C_{14}$ primary alcohols containing 3–5 moles of ethylene oxide per mole of alcohol.

Another class of nonionic surfactants comprises alkyl polyglucoside compounds of general formula $$RO(C_nH_{2n}O)_tZ_x$$

wherein Z is a moiety derived from glucose; R is a saturated hydrophobic alkyl group that contains from 12 to 18 carbon atoms; t is from 0 to 10 and n is 2 or 3; x is from 1.3 to 4, the compounds including less than 10% unreacted fatty alcohol and less than 50% short chain alkyl polyglucosides. Compounds of this type and their use in detergent are disclosed in EP-B 0 070 077, 0 075 996 and 0 094 118.

Also suitable as nonionic surfactants are polyhydroxy fatty acid amide surfactants of the formula

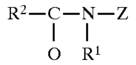

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or alkenyl chain such as coconut alkyl or mixtures thereof, and Z is derived from a reducing sugar such as glucose, fructose, maltose, lactose, in a reductive amination reaction.

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein. Suitable polycarboxylates builders for use herein include citric acid, preferably in the form of a water-soluble salt, derivatives of succinic acid of the formula R-CH(COOH)CH2(COOH) wherein R is $C_{10-20}$ alkyl or alkenyl, preferably $C_{12-16}$, or wherein R can be substituted with hydroxyl, sulfo sulfoxyl or sulfone substituents. Specific examples include lauryl succinate , myristyl succinate, palmityl succinate2-dodecenylsuccinate, 2-tetradecenyl succinate. Succinate builders are preferably used in the form of their water-soluble salts, including sodium, potassium, ammonium and alkanolammonium salts. Other suitable polycarboxylates are oxodisuccinates and mixtures of tartrate monosuccinic and tartrate disuccinic acid such as described in U.S. Pat. No. 4,663,071. Especially for the liquid execution herein, suitable fatty acid builders for use herein are saturated or unsaturated $C_{10-18}$ fatty acids, as well as the corresponding soaps. Preferred saturated species have from 12 to 16 carbon atoms in the alkyl chain. The preferred unsaturated fatty acid is oleic acid. Another preferred builder system for liquid compositions is based on dodecenyl succinic acid. Other suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 10% to 80% by weight of the composition preferably from 20% to 70% and most usually from 30% to 60% by weight.

Other components used in detergent compositions may be employed, such enzymes and stabilizers or activators therefore, soil-suspending agents soil-release agents, optical brighteners, abrasives, bactericides, tarnish inhibitors, coloring agents, and perfumes. Especially preferred are combinations with enzyme technologies which also provide a type of color care benefit. Examples are cellulase for color maintenance/ rejuvenation.

The following examples are meant to exemplify compositions of the present inventions, but are not necessarily meant to limit the scope of the invention. In these examples, a loop neutralizer was employed as substantially as hereinabove described. All percentages are by weight unless otherwise stated;

Example (1–26)

Alkyl sulfate solutions were prepared according to the process of the present invention. The structure of each composition was assessed at room temperature and the results are given in Table 1 and graphically expressed in FIG. 1.

Example 27

The neutralization reaction was carried out under the following reaction conditions: A 70% active alkylsulfate solution was prepared according to the process of the present invention.

The composition, thus obtained is an isotropic freeflowing liquid at room temperature.

| | |
|---|---|
| Natural alcohol C12/14 | 42.60% |
| monoethanolamine (MEA) | 13.31% |
| 1,2 Propane diol | 28.03% |
| Production rate | 2350 kg/h |
| Propane diol | 658.5 kg/h or 634 1/h |
| MEA | 317.25 kg/h (12 mm pump settings) |

The capacity of this loop reactor is fixed by the capacity of the sulfation unit or the flow rate at which the loop reactor is fed with acid mix (alkyl sulfuric acid).

Start - stop procedure

The loop reactor was drained completely and flushed with propane diol to remove all water (NH4-AS was produced prior to the MEA-AS trial).

The loop was filled up with propane diol (20').

Gear pump switched on.

MEA addition during 3' without propane diol addition. With the MEA pump settings at 317.25 kg/h this means that MEA is now present at a 10% excess in the loop reactor.

Propane diol and MEA are circulated for 3' to obtain a homogeneous mixture.

Once homogeneous the acid mix (alkyl sulfuric acid) is fed into the loop together with MEA/propane diol.

Process conditions:

| Time (min.) | Act. | pH as is | pH of 1% | Excess MEA | T (°C.) in | out (°C.) |
|---|---|---|---|---|---|---|
| 10' | — | 9.0 | — | 1.378 | | |
| 20' | — | 8.1 | — | 1.080 | 80 | 69 |
| 30' | — | 7.4 | — | 1.080 | 78 | 69 (MEA adjusted to 12.5 mm) |

-continued

| Time (min.) | Act. | pH as is | pH of 1% | Excess MEA | T (°C.) in | out (°C.) |
|---|---|---|---|---|---|---|
| 40' | 70.2 | 7.6 | — | 1.480 | 74 | 65 |
| 50' | — | 7.7 | 8.9 | 1.410 | 73 | 65 |
| 1h | — | 7.7 | — | 1.390 | 74 | 65 |
| 1h10' | 71.7 | 7.6 | 8.8 | 1.220 | 74 | 65 |
| 1h20' | — | 7.6 | — | 1.200 | 74 | 65 |
| 1h30' | — | 7.6 | 8.8 | 1.150 | 73 | 65 |
| 1h40' | — | 7.5 | — | 1.170 | 73 | 65 |
| 1h50' | 69.9 | 7.5 | — | 1.146 | 73 | 65 |
| 2h | — | 7.5 | — | 1.180 | 73 | 65 |
| 2h10' | — | 7.5 | — | 1.160 | 73 | 65 |
| Mix tank | 67.9 | — | 8.9 | 1.30 | 65 | 40 (mix cooled) |

The outlet temperature setting of the heat exchanger are at the high side to prevent any possible high viscosity during these first trials. Later productions are set at a heat exchanger outlet temperature of about 40° C.

The shut down procedure is done in reversed order: remove the acid mix first, wind down the MEA and propane diol pump settings.

RESULTS:

The phase diagram according to Table I indicates that different phases can be obtained when making a ternairy mixture of water/propanediol/monoethanolaminealkylsulfate. More in particular, the phase diagram shows that a high active freeflowing isotropic liquid can be obtained when compositions according to the present invention are made without the need of adding cosolvents or viscosity modifiers.

FIG. 1: PHASE DIAGRAM MEA-AS/WATER/1,2 PROP.DIOL
MEA-AS: sourced from $C_{12/14}$ natural alcohol

| SAMPLE | MEA-AS | PDIOL | WATER | PHASE |
|---|---|---|---|---|
| 1 | 80 | 10 | 10 | G |
| 2 | 70 | 10 | 20 | G |
| 3 | 70 | 20 | 10 | G |
| AA | 70 | 30 | 0 | I |
| 3A3A | 66 | 28 | 6 | I/G |
| 44 | 60 | 10 | 30 | G |
| 55 | 60 | 20 | 20 | G |
| 5A | 60 | 26 | 14 | G |
| 5B | 60 | 28 | 12 | I/G |
| 6 | 60 | 30 | 10 | I |
| 6A | 54 | 23 | 23 | G |
| 6B | 54 | 26 | 20 | I/G |
| 6C | 54 | 36 | 10 | I |
| 6D | 54 | 37 | 9 | I |
| 7 | 50 | 10 | 40 | G |
| 7A | 50 | 15 | 35 | I/G |
| 8 | 50 | 20 | 30 | I |
| 8A | 50 | 25 | 25 | I |
| 9 | 50 | 30 | 20 | I |
| 9A | 50 | 35 | 15 | I |
| 10 | 50 | 40 | 10 | I |
| 10A | 46 | 30 | 24 | I |
| 10B | 46 | 34 | 20 | I |
| 10B1 | 46 | 37 | 17 | I |
| 10C | 46 | 40 | 14 | I |
| 10D1 | 44 | 16 | 40 | I/G |
| 10D | 44 | 30 | 26 | I |
| 11 | 40 | 10 | 50 | I/G |
| 12 | 40 | 20 | 40 | I |
| 13 | 40 | 30 | 30 | I |
| 14 | 40 | 40 | 20 | I |
| 15 | 40 | 50 | 10 | I |
| 15A | 35 | 17 | 48 | I |
| B | 30 | 0 | 70 | I |
| 16 | 30 | 10 | 60 | I |
| 17 | 30 | 20 | 50 | I |

-continued

FIG. 1: PHASE DIAGRAM MEA-AS/WATER/1,2 PROP.DIOL
MEA-AS: sourced from $C_{12/14}$ natural alcohol

| SAMPLE | MEA-AS | PDIOL | WATER | PHASE |
|---|---|---|---|---|
| 18 | 30 | 30 | 40 | I |
| 19 | 30 | 40 | 30 | I |
| 20 | 30 | 50 | 20 | I |
| 21 | 30 | 60 | 10 | I |
| 22 | 20 | 10 | 70 | I |
| 23 | 20 | 20 | 60 | I |
| 24 | 20 | 30 | 50 | I |
| 25 | 20 | 40 | 40 | I |
| 26 | 20 | 50 | 30 | I |

PHASE I = ISOTROPIC
G = GEL-structured phase
I/G = MIX OF ISOTROPIC AND STRUCTURED PHASES

What is claimed is:

1. A process for producing high active alkyl sulphate solutions comprising the steps of:

(a) premixing an alcohol or an alkoxylated nonionic surfactant of the formula $R(OC_2H_4)_nOH$, wherein R is a $C_{12}$-$C_{18}$ alkyl group and n is from 1 to 12, with an organic amine to form a premix; and (b) adding to the premix, $C_{12}$-$C_{18}$ alkyl sulfuric acid, to produce a neutralized product additive having substantially no water wherein the weight ratio of the additive to the premix is from 0.5:1 to 9:1.

2. A process according to claim 1 wherein the alkylsulfuric acid is a derived from $C_{12}$-$C_{14}$ natural fatty alcohol.

3. A process according to claim 1 wherein the alkylsulfuric acid is derived from a $C_{12}$-$Cl_5$ synthetic fatty alcohol.

4. A process according to claim 1 wherein the organic amine is selected from an alkylamine , an alkanolamine or mixtures thereof.

5. A process according to claim 4 wherein the organic amine is monoethanolamine.

6. A process according to claim 1 wherein the alcohol is selected from propanediol, ethanol or mixtures thereof.

7. A process according to claim 1 wherein the alkyl sulfuric acid is present as a mixture with alkyl ether sulfuric acids.

8. A process according to claim 1 wherein the neutralization is carried out in a continuous loop system.

* * * * *